United States Patent [19]

Rayle et al.

[11] Patent Number: 5,886,210

[45] Date of Patent: Mar. 23, 1999

[54] METHOD FOR PREPARING AROMATIC COMPOUNDS

[75] Inventors: Heather Lynnette Rayle, North Wales; Randall Wayne Stephens, Perkasie, both of Pa.

[73] Assignee: Rohm and Haas Company, Philadelphia, Pa.

[21] Appl. No.: 876,211

[22] Filed: Jun. 16, 1997

Related U.S. Application Data

[60] Provisional application No. 60/024,398, Aug. 22, 1996.

[51] Int. Cl.$^6$ .................................................. C07C 69/76
[52] U.S. Cl. ........................ 560/103; 562/493; 561/184; 568/323
[58] Field of Search ........................... 560/103; 562/493; 564/184; 568/323

[56] References Cited

U.S. PATENT DOCUMENTS

| 3,423,475 | 1/1969 | Weinstock et al. . |
| 4,603,201 | 7/1986 | Takeshiba et al. . |
| 4,981,999 | 1/1991 | O'Reilly et al. . |

FOREIGN PATENT DOCUMENTS

| 557878 A1 | 9/1993 | European Pat. Off. . |
| 2810267 A | 9/1978 | Germany . |
| 3615762 A | 5/1985 | Germany . |
| 53009321 | 1/1978 | Japan . |
| 53012879 | 2/1978 | Japan . |
| 53111033 | 9/1978 | Japan . |
| 55036434 | 3/1980 | Japan . |
| 60016965 | 1/1985 | Japan . |

OTHER PUBLICATIONS

W. T. Smith, Jr., *J. Am. Chem. Soc.*, 71, 2855 (1949).
Jojima et al., *Bulletin of the Chemical Society of Japan*, 52(8), 2441–2 (1979).
Weinstock et al., *Organic Preparations and Procedures, Inc.*, 13(2), 103–108 (1981).

Primary Examiner—Paul J. Killos
Attorney, Agent, or Firm—Clark R. Carpenter

[57] ABSTRACT

A method for synthesizing aromatic compounds by selectively dehalogenating aromatic starting materials is provided. Compounds may be prepared which are substituted with fluoro, chloro or bromo. The method may be used to remove halogen atoms from sites at which halogenation is not desired, and to form substantially pure halogenated compounds from mixtures of starting materials. The method uses a copper containing dehalogenation agent and an acid with the dehalogenation being controlled by a substituent such as a carboxylic acid, amide, ester, aldehyde, ketone or cyano on the aromatic ring.

23 Claims, No Drawings

METHOD FOR PREPARING AROMATIC COMPOUNDS

The present invention relates to a method for preparing aromatic compounds. In particular, the present invention relates to a method for preparing aromatic compounds having a halogen atom at one or more selected sites. The present invention also provides a method for removal of halogen atoms from sites at which the halogen atoms are not desired. Under some conditions, the method of the present invention may be used to remove all halogen substituents from halogenated aromatic compounds.

Halogenation reactions are integral steps in synthetic pathways for the preparation of many aromatic organic compounds. However, halogenation reactions may produce mixtures having undesired degrees of halogenation, or halogen atoms at sites other than those intended. Selective halogenation, meaning halogenation at selected sites on aromatic compounds, may be accomplished by the use of aromatic starting materials containing "directing groups". A directing group is a moiety which, when it is a substituent on an aromatic ring, affects the electron distribution in the aromatic ring thereby determining at which positions aromatic substitution is likely to occur. Halogenation at specific sites may be difficult, however, either when no directing groups are present or when there are present directing groups which are not sufficiently active for the addition of more than one halogen atom. Selective halogenation may also be difficult when multiple directing groups are present which may effect substitution in a random manner on the different remaining positions of the aromatic ring.

In an effort to solve these problems, various catalysts have been used in the preparation of halogenated aromatic compounds. For instance, Becher et al. (DE 3,615,762) describes a method in which iron(III) chloride is used as a catalyst for the preparation of chlorinated aromatic compounds from 4-alkylbenzoyl chlorides. However, the method of Becher et al. may not provide sufficient yield and selectivity for some applications and, consequently, the product mixture may be difficult to purify.

In an alternative method, aluminum chloride has been used as a catalyst in the preparation of 4-(3,5-dihalophenyl)-4-oxobutyric acids and butenoic acids {JP 5-3111033, 5-3009321 and 5-3012879; Jojima et al., *Bulletin of the Chemical Society of Japan*, 52 (8), 2441–2 (1979)}. However, the reported yields were about 52 percent or less. It would be beneficial to have a method for preparing halogenated compounds with a higher yield while maintaining site selectivity. Also, the aluminum chloride catalyst is not reusable and must be quenched at the end of each reaction, which generates hydrochloric acid and waste acidic aluminum salts. The acidic aluminum waste must then be treated and disposed of which adds to the cost of a process.

Chlorinated aromatic compounds have also been prepared by chlorination and subsequent partial dechlorination of aromatic compounds substituted with nitro and sulfonic acid groups {W. T. Smith, Jr., *J. Am. Chem. Soc.* 71, 2855 (1949); U.S. Pat. No. 3,423,475; and JP 6-16,965 (1985)}. The presence of the nitro and sulfonic acid groups in the final halogenated product is often undesirable, so several additional reaction steps may be required to remove these functionalities or replace them with other functional groups.

Chlorinated phthalic acids and anhydrides have been partially dehalogenated in the presence of metals such as zinc under strongly basic conditions (U.S. Pat. No. 4,981,999). However, some directing groups may not be stable to the required basic conditions. The procedure does not selectively dehalogenate brominated aromatic compounds since all the bromine atoms are removed under these conditions. Additionally, fluorine atoms are not stable under the reaction conditions as they may be replaced by hydroxyl groups.

Therefore, there continues to be a need for new processes by which halogenated aromatic compounds can be made with an acceptable yield for most applications, with reduced waste handling, and in which the sites of halogenation can be controlled for enhanced selectivity. The present invention overcomes the deficiencies in known methods for making halogenated aromatic compounds and provides control of halogenation by the use of directing groups. Furthermore, the present invention provides a method for the selective dehalogenation of halogenated aromatic compounds to form either new halogenated aromatic compounds or non-halogenated aromatic compounds.

It has been surprisingly found that certain halogenated aromatic compounds, containing a directing group, may be selectively dehalogenated using a dehalogenation agent which comprises copper metal or compounds containing copper. The copper dehalogenation agent may be present in a catalytic quantity under some reaction conditions, for example, when a carboxylic acid and an amine solvent are present. Selectivity in the method of the present invention is provided by the removal of halogen atoms from selected positions in a halogenated aromatic compound containing a directing group. The method of the present invention typically provides a desired product yield of about 70 percent or greater.

The method of the present invention permits the use of aromatic compounds having directing groups such as carboxylic acids, ketones and esters which may be used in subsequent reactions or which may be desired in the reaction product. This presents an advantage over known methods in which nitro or sulfonic acid groups are used as directing groups and which may require subsequent steps to replace these functional groups with carbon-based substituents. The method of the present invention is complementary to the known method of partially dehalogenating phthalic acid derivatives in which the regioselectivity of the dehalogenation is such that chlorine atoms located ortho to the carboxylic acid-derived substituents are least readily dehalogenated. In the method of the present invention, halogens located ortho to the carboxylic acid-derived substituent are selectively removed, while halogens located elsewhere are typically unaffected. Furthermore, the present invention provides advantages over the known procedure for dehalogenation of phthalic acid derivatives in that the current invention provides for selective removal of bromine atoms. Moreover, if fluorine atoms are present, they are not removed since they are stable to the reaction conditions; thus, they are not displaced as in the prior art method.

The method of the present invention also simplifies the separation of mixtures of compounds following synthesis compared to known synthetic methods. For example, mixtures of halogenated compounds may be converted to a single halogenated compound of about 95% or higher purity.

Thus, in summary, the present invention provides a method for preparing selectively halogenated aromatic compounds, which may contain other desired functional moieties, with a reduced number of steps and reduced waste disposal procedures as compared with conventional synthetic methods for forming such compounds. The method also reduces the need for separation steps, such as fractional distillation, to isolate a desired halogenated compound from a mixture of halogenation reaction products. The method can also provide, if desired, a convenient means to form a non-halogenated aromatic compound by the selective dehalogenation method described herein.

The present invention provides a method for preparing an aryl or a heteroaryl compound by selectively removing halogen atoms from a halogenated aryl or heteroaryl compound through heating a reaction mixture comprising (i) at least one aryl or heteroaryl compound possessing a Z directing group and one or two halo groups independently selected from chloro, bromo and iodo which are ortho to said Z group, or a further substituted aryl or heteroaryl compound possessing a Z directing group and one or two halo groups independently selected from chloro, bromo and iodo which are ortho to said Z group, (ii) from about 0.01 to about 5.0 molar equivalents, per equivalent of halo group to be removed, of a copper containing dehalogenation agent, and (iii) at least about 1.0 molar equivalent, per equivalent of halo group to be removed, of one or more acids selected from the group consisting of aliphatic $(C_1-C_{10})$ carboxylic acids, aliphatic $(C_2-C_{10})$dicarboxylic acids, aryl carboxylic acids, aryl dicarboxylic acids, aqueous inorganic acids, sulfonic acids and mixtures thereof; wherein the Z directing group is $CO_2R^{10}$, $CONR^{11}R^{12}$, $COR^{13}$ or cyano, $R^{10}$, $R^{11}$ and $R^{12}$ are each independently a hydrogen atom, $(C_1-C_6)$alkyl, aryl or substituted aryl, and $R^{13}$ is a hydrogen atom, $(C_1-C_6)$alkyl, substituted $(C_1-C_6)$alkyl, aryl or substituted aryl.

As used herein, the term "alkyl" refers to straight $(C_1-C_8)$ and branched $(C_3-C_8)$ aliphatic hydrocarbon chains, for example, methyl, ethyl, n-propyl, isopropyl, n-butyl, and tert-butyl. "Substituted alkyl" refers to alkyl groups substituted with, for example, hydroxy, mercapto, $(C_1-C_4)$alkoxy, $(C_1-C_4)$alkylthio, hydroxy$(C_1-C_4)$alkyl, $(C_3-C_6)$ cycloalkyl, aryl, substituted aryl, heteroaryl, substituted heteroaryl, aryloxy, substituted aryloxy, heteroaryloxy, substituted heteroaryloxy, aryl$(C_1-C_4)$alkyl in which either the alkyl moiety or both may contain substituents, heteroaryl$(C_1-C_4)$alkyl, substituted heteroaryl $(C_1-C_4)$alkyl, aryl$(C_1-C_4)$alkoxy, substituted aryl$(C_1-C_4)$alkoxy, heteroaryl$(C_1-C_4)$alkoxy, substituted heteroaryl$(C_1-C_4)$alkoxy, aryloxy$(C_1-C_4)$alkyl, substituted aryloxy$(C_1-C_4)$alkyl, acyloxy, nitro, thio, NR'R", NHCOR', NHCOOR', CONR'R", COOR', OSO$_2$R', SO$_2$R', and COR', in which R' and R" are independently selected from a hydrogen atom, $(C_1-C_6)$alkyl, $(C_1-C_4)$alkoxy, $(C_1-C_4)$ alkylthio, $(C_3-C_6)$cycloalkyl, $(C_3-C_6)$cycloalkyl$(C_1-C_4)$ alkyl, phenyl, benzyl and phenethyl, wherein the phenyl, benzyl and phenethyl may be substituted with $(C_1-C_4)$alkyl or $(C_1-C_4)$alkoxy.

The term "cycloalkyl" refers to a closed saturated cyclic $(C_3-C_6)$ moiety and includes, for example, cyclopropyl and cyclohexyl. Cycloalkyl groups may be substituted and optional substituents include those listed above as optional substituents for alkyl groups.

The term "aryl" refers to an aromatic ring system, for example, phenyl, 1-naphthyl, 2-naphthyl, anthryl, phenanthryl and the like.

The term "heteroaryl" refers to aromatic heterocyclic groups. Heteroaryl rings and the heteroaryl moieties of other groups, such as heteroaryloxyalkyl and heteroarylalkyl, are typically 5 or 6 membered aromatic rings containing one or more O, N, or S atoms which may be fused to one or more other aromatic, heteroaromatic or heterocyclic rings such as a benzene ring. Examples of heteroaryl groups include, but are not limited to, thienyl, furyl, pyrrolyl, triazolyl, thiazolyl, oxazolyl, isoxazolyl, thiazolyl, isothiazolyl, pyridyl, pyrimidinyl, pyrazinyl, pyridazinyl, triazinyl, benzofuranyl, benzothienyl, indolyl, quinazolinyl, acridinyl, purinyl and quinoxalinyl.

Substituents which may be present in substituted aryl and substituted heteroaryl moieties may include one or more $(C_1-C_6)$alkyl, hydroxy, mercapto, $(C_1-C_4)$alkoxy, $(C_1-C_4)$ alkylthio, hydroxy$(C_1-C_4)$alkyl, $(C_1-C_4)$alkoxy$(C_1-C_4)$ alkyl, $(C_3-C_6)$cycloalkyl, aryl, substituted aryl, heteroaryl, substituted heteroaryl, aryloxy, substituted aryloxy, heteroaryloxy, substituted heteroaryloxy, aryl$(C_1-C_4)$alkyl in which either the aryl moiety, the alkyl moiety or both may contain substituents, heteroaryl$(C_1-C_4)$alkyl, substituted heteroaryl$(C_1-C_4)$alkyl, aryl$(C_1-C_4)$alkoxy, substituted aryl $(C_1-C_4)$alkoxy, heteroaryl$(C_1-C_4)$alkoxy, substituted heteroaryl$(C_1-C_4)$alkoxy, aryloxy$(C_1-C_4)$alkyl, substituted aryloxy$(C_1-C_4)$alkyl, acyloxy, nitro, thio, NR'R", NHCOR', NHCOOR', CONR'R", COOR', OSO$_2$R', SO$_2$R', and COR', in which R' and R" are independently selected from hydrogen, $(C_1-C_6)$alkyl, $(C_1-C_4)$alkoxy, $(C_1-C_4)$alkylthio, $(C_3-C_6)$cycloalkyl, $(C_3-C_6)$cycloalkyl$(C_1-C_4)$alkyl, phenyl, benzyl and phenethyl wherein the phenyl, benzyl and phenethyl may substituted on the phenyl portion of the moiety with $(C_1-C_4)$alkyl or $(C_1-C_4)$alkoxy.

Aliphatic $(C_1-C_{10})$ carboxylic acids are compounds having the formula $R^{15}CO_2H$ wherein $R^{15}$ is a hydrogen atom or $(C_1-C_9)$alkyl and include, for example, formic acid, acetic acid, propionic acid, valeric acid, pivalic acid and the like.

Aliphatic $(C_2-C_{10})$ dicarboxylic acids are compounds having the formula $HO_2C(CHR^{16})_nCO_2H$ wherein $R^{16}$ is a hydrogen atom when n is 0–8 or $(C_1-C_7)$alkyl when n is 1 and include, for example, oxalic acid, succinic acid, malonic acid and the like.

Aryl carboxylic acids include, for example, benzoic acid, 1-naphthoic acid, 2-naphthoic acid, 9-phenanthroic acid and the like.

Aryl dicarboxylic acids include, for example, phthalic acid, isophthalic acid, terephthalic acid, naphthalenedicarboxylic acid and the like.

Sulfonic acids include, for example, benzenesulfonic acid, p-toluenesulfonic acid, methanesulfonic acid, ethanesulfonic acid, 1-naphtlhalenesulfonic acid, 2-naphthalenesulfonic acid and the like.

Any of the above described aliphatic $(C_1-C_{10})$ carboxylic acids, aliphatic $(C_2-C_{10})$ dicarboxylic acids, aryl carboxylic acids, aryl dicarboxylic acids and sulfonic acids may be substituted and the substituents are not critical provided that none of the substituents are halogen atoms.

In a preferred embodiment of this invention, the aryl or heteroaryl compound, possessing a Z directing group and one or two halo groups independently selected from chloro, bromo and iodo which are ortho to said Z group, is phenyl, 1-naphthyl, 2-naphthyl, anthryl, phenanthryl, thienyl, furyl, pyrrolyl, triazolyl, thiazolyl, oxazolyl, isoxazolyl, thiazolyl, isothiazolyl, pyridyl, pyrimidinyl, pyrazinyl, pyridazinyl, triazinyl, benzofuranyl, benzothienyl, indolyl, quinazolinyl, acridinyl, purinyl or quinoxalinyl; or the further substituted aryl or heteroaryl compound, possessing a Z directing group and one or two halo groups independently selected from chloro, bromo and iodo which are ortho to said Z group, is phenyl, 1-naphthyl, 2-naphthyl, anthryl, phenanthryl, thienyl, furyl, pyrrolyl, triazolyl, thiazolyl, oxazolyl, isoxazolyl, thiazolyl, isotlhiazolyl, pyridyl, pyrimidinyl, pyrazinyl, pyridazinyl, triazinyl, benzofuranyl, benzothienyl, indolyl, quinazolinyl, acridinyl, purinyl or quinoxalinyl.

In a more preferred embodiment of this invention, the aryl compound is a substituted phenyl having the formula (I)

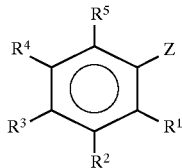

wherein $R^1$, $R^2$, $R^3$, $R^4$ and $R^5$ are each independently a hydrogen atom, $(C_1-C_8)$alkyl, substituted $(C_1-C_8)$alkyl, $(C_3-C_6)$cycloalkyl, substituted $(C_3-C_6)$cycloalkyl, aryl, substituted aryl, $CH_2OR^6$, $NR^7R^{10}$, $OR^8$, $SR^9$, heteroaryl, substituted heteroaryl, fluoro, chloro, bromo or iodo, provided that at least one of $R^1$ and $R^5$ is chloro, bromo or iodo, the Z directing group is $CO_2R^{10}$, $CONR^{11}R^{12}$, $COR^{13}$ or cyano, $R^6$, $R^8$ and $R^9$ are each independently a hydrogen atom, $(C_1-C_6)$alkyl, aryl, substituted aryl or $COR^{14}$, $R^7$, $R^{10}$, $R^{11}$ and $R^{12}$ are each independently a hydrogen atom, $(C_1-C_6)$alkyl, aryl or substituted aryl, $R^{13}$ is a hydrogen atom, $(C_1-C_6)$alkyl, substituted $(C_1-C_6)$alkyl, aryl or substituted aryl, and $R^{14}$ is $(C_1-C_6)$alkyl or aryl.

In a still more preferred embodiment of this invention using the substituted phenyl of formula (I), $R^1$ and $R^5$ are each independently a hydrogen atom, $(C_1-C_8)$alkyl, substituted $(C_1-C_8)$alkyl, aryl, substituted aryl, fluoro, chloro, bromo or iodo, provided that at least one of $R^1$ and $R^5$ is chloro, bromo or iodo, $R^2$, $R^3$ and $R^4$ are each independently a hydrogen atom, $(C_1-C_8)$alkyl, aryl, substituted $(C_1-C_8)$alkyl, substituted aryl, $NR^7R^{10}$, fluoro, chloro or bromo, Z is $CO_2R^{10}$, $CONR^{11}R^{12}$ or $COR^{13}$, $R^7$ and $R^{10}$ are each independently a hydrogen atom, $(C_1-C_6)$alkyl, aryl and substituted aryl, $R^{11}$ and $R^{12}$ are each independently $(C_1-C_6)$alkyl, aryl or substituted aryl and $R^{13}$ is $(C_1-C_6)$alkyl, substituted $(C_1-C_6)$alkyl, aryl or substituted aryl.

In a still more preferred embodiment of this invention using the substituted phenyl of formula (I), $R^1$ and $R^5$ are each independently a hydrogen atom, $(C_1-C_8)$alkyl, chloro or bromo, provided that at least one of $R^1$ and $R^5$ is chloro or bromo, $R^2$, $R^3$ and $R^4$ are each independently a hydrogen atom, $(C_1-C_8)$alkyl, aryl, fluoro, chloro or bromo, Z is $CO_2R^{10}$, and $R^{10}$ is a hydrogen atom, $(C_1-C_6)$alkyl, aryl or substituted aryl.

The composition of the groups $R^{10}$, $R^{11}$, $R^{12}$, $R^{13}$ and $R^{14}$ is not critical to the method of the invention and may be selected according to the functional groups desired in the final compound.

Under certain reaction conditions, certain functional groups will undergo secondary reactions during the dehalogenation reaction or the work-up procedure. For example, a nitrile or acyl halide group may convert to a carboxylic acid. As will be recognized by a person of ordinary skill in the art, such secondary reactions may be useful in forming desired functional groups.

The method of the present invention allows the preparation of halogenated aromatic compounds in which the position of the one or more halogen atoms may be pre-selected. In particular, the method of the present invention allows for selection of the position of chloro and bromo. The method is also useful for the removal of an iodo group if selectivity in the removal of the iodo from particular positions on the aromatic ring is not required. The method is also useful in that certain halogenated aromatic starting materials may be used to form aromatic compounds having no halogen substituents.

The method of the present invention may be used to prepare aromatic halogenated compounds substituted with at least one halogen atom selected from fluoro, chloro and bromo. Since fluoro is not affected by the method of the present invention, it may be present and may be in any one or more position on the aromatic ring. Up to five halo substituents may be present, not necessarily all the same. Alternatively, there may be also present on the ring substituents other than halo substituents.

When selective removal of chloro is desired, it is required that at least one chloro (the chloro which is to be removed) be in the ortho position with respect to the Z group. However, non-selective removal may result from prolonged reaction in the presence of an excess of the copper source if a second chloro is in the meta or para position relative to the Z group. When removal of bromo is desired, the bromo to be removed may be located in the ortho or para position with respect to Z. However, if more than one bromo is to be removed, it is preferred that at least one bromo to be removed is located ortho to the Z group. If two chloro, two bromo or one chloro and one bromo substituent are located ortho to the Z group, both halo substituents will be removed.

More than one Z group may be present. The presence of more than one Z group may increase the extent of dehalogenation and may affect the selectivity of the method. For example, a ring containing three halo substituents and two Z groups in alternating positions on the ring will have all halo substituents removed, if the halo substituents present are selected from chloro, bromo and iodo. A ring containing two Z groups para to each other and four halo substituents on the remaining positions may also be completely dehalogeniated, if the halo substituents present are selected from chloro, bromo and iodo.

Materials required in the method of the present invention include at least one halogenated aromatic compound substituted with one or more Z groups as described hereinabove, a dehalogenation reagent comprising copper metal or a copper containing compound, and at least one carboxylic or dicarboxylic acid, a sulfonic acid or an aqueous acid. Copper metal or a copper(I) compound are usually employed in such cases. A copper(I) compound is a compound containing ionic copper in which the copper is in the +1 oxidation state. Examples of well-known copper(I) compounds include, but are not limited to, copper(I) chloride, copper(I) bromide, and copper(I) oxide. In certain situations, it is advantageous to employ one or more solvents to better effect the method of the present invention. If the one of the solvents is an amine type, the dehalogenation agent may further embrace copper (II) type compounds. A copper(II) compound is a compound containing ionic copper in which the copper is in the +2 oxidation state. Examples of well-known copper(II) compounds include, but are not limited to, copper(II) acetate, copper(II) chloride, copper(II) bromide, copper(II) oxide and copper(II) sulfate.

A solvent is required under conditions where the starting material or the copper source is insoluble or the carboxylic acid reagent is not fluid at the reaction temperature. Such conditions may occur when an aqueous inorganic acid is used. Dicarboxylic acids or higher-boiling carboxylic acids may require the use of a solvent because they may not be fluid at the reaction temperature. A solvent may also be added after the reaction is complete as the reaction mixture cools, if the carboxylic or dicarboxylic acid reagent is not fluid at room temperature.

The method of the present invention is carried out at a temperature of at least 70° C. It is preferred that the reaction temperature be from 95° C. to 220° C., more preferably from 105° C. to 150° C. The reaction pressure is not critical, but pressures of about 1 atm (101 kiloPascal, kP) are usually employed for convenience.

The composition of the halogenated aromatic compound used in the method of the present invention is determined by the product desired. Examples of halogenated aromatic compounds include, but are not limited to, methyl 2,5-dichlorobenzoate, 2,4-dichlorobenzamide, 2,4-dichloroacetoplhenone, 2,3-dichlorobenzoic acid and methyl 2,5-dichloro-4-methylbenzoate.

Other halogenated aromatic compounds for use as starting materials may be synthesized according to methods known to those skilled in the art. For example, an aromatic compound containing a directing group Z may be treated with a halogen source to produce one or more halogenated aromatic compounds as shown:

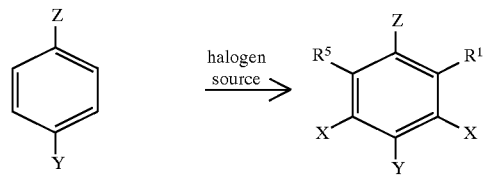

Z = as defined herein
Y = (C₁–C₆)alkyl, halo, (C₁–C₄)alkoxy, H, etc.
X = halo

R¹ = R⁵ = H
R¹ = X, R⁵ = H
R¹ = R⁵ = X

As an example, methyl 4-chlorobenzoate may be chlorinated using chlorine gas in the presence of a Lewis acid catalyst, such as aluminum chloride or iron(III) chloride, to produce a mixture of three chlorinated compounds. This mixture may then be selectively dehalogenated to produce methyl 3,4,5-trichlorobenzoate as shown:

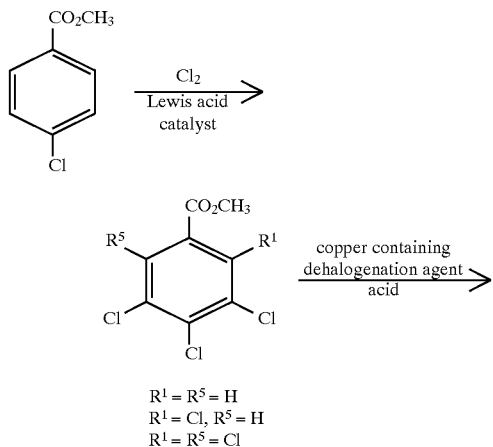

R¹ = R⁵ = H
R¹ = Cl, R⁵ = H
R¹ = R⁵ = Cl

-continued

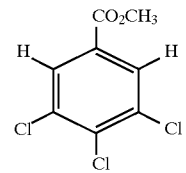

The amount of halogenated aromatic compound is not critical provided the reaction mixture is fluid. Generally the amount of halogenated aromatic compound may be from 5 percent to 50 percent by weight, based on the combined weight of the halogenated compound and acid. Preferably, the amount of halogenated aromatic compound is from 20 percent to 40 percent.

As discussed previously, a copper containing dehalogenation agent is required for selectivity according to the method of the present invention. The copper containing dehalogenation agent may be metallic copper or a copper(I) compound if no amine containing solvent is present. If an amine containing solvent is present, a copper(II) compound may also be utilized. The copper containing dehalogenation agent is preferably added in powder form. Examples of copper(I) compounds useful in the method of the present invention include, but are not limited to, copper(I) oxide, copper(I) bromide and copper(I) chloride. Examples of copper(II) compounds useful in the method of the present invention include, but are not limited to, copper(II) acetate, copper(II) chloride, copper(II) bromide, copper(II) oxide and copper(II) sulfate. The amount of copper containing dehalogenation agent is generally from about 0.5 to about 5 equivalents of copper per equivalent of halo group to be removed, preferably from about 1.0 to about 4.0 equivalents and more preferably from about 1.0 to about 3.0 equivalents. When an amine containing solvent is present, the amount of copper containing delhalogenation agent used is from about 0.01 to about 2.0 equivalents of copper per equivalent of halo group to be removed and preferably from about 0.1 to about 1.0 equivalent. Alternatively, a conventional solvent in the presence of a polymer containing an amine functionality such as poly(4-vinylpyridine) may also be used with a lower level of a copper containing dehalogenation agent.

One or more carboxylic acids can be used in the method of the present invention. The one or more carboxylic acids may be aromatic or aliphatic. Examples of aliphatic carboxylic acids useful in the method of the present invention include, but are not limited to, acetic acid, propionic acid, valeric acid, pivalic acid and butyric acid. Examples of aromatic carboxylic acids useful in the method of the present invention include, but are not limited to, benzoic acid and toluic acid. Dicarboxylic acids may also be used. Examples of dicarboxylic acids include, but are not limited to, oxalic acid, succinic acid, malonic acid and phthalic acid. A mixture of acids may be used. The total amount of carboxylic acid is preferably at least one molar equivalent per mole of halogen to be removed.

Alternatively, a water soluble acid can be used in the method of the present invention. Examples of such acids include, but are not limited to, sulfuric acid, hydrochloric acid, methanesulfonic acid and p-toluenesulfonic acid. However, more copper may be required with the use of an aqueous reaction medium than when a carboxylic acid is employed. The use of water soluble acids also may limit the types of functional groups which may be present on the starting aromatic compounds since some functional groups may undesirably react with the aqueous acid. Additionally, the reaction may take longer to complete when an aqueous medium is used. The concentration of water soluble acids, if used, is not critical. A minimum of 5 weight percent, based on the combined weight of the halogenated aromatic compound and the aqueous medium, is preferred. However, in many cases a solvent may be required in order to obtain a fluid mixture.

An excess of aqueous or organic acid may be present with no adverse effect on the reaction.

Optionally, a solvent may be used in addition to the one or more carboxylic acid, dicarboxylic acid or aqueous acid. Examples of useful solvents include, but are not limited to, xylene, toluene, ethyl acetate, butyl acetate, mesitylene, octane, decane, anisole, nitrobenzene, methoxyethyl ether, dimetlhyl sulfoxide, N,N-dimethylformamide, pyridine, pyrrolidline, 2-pyrrolidinone, pyrrole, piperidine, piperazine, quinoline, acetonitrile, valeronitrile, triethylamine, triisobutylamine, tripropylamine, diisopropylamine, chlorobenzene, dichlorobenzene, N,N,N', N'-tetramethylethylenediamine, 4-picoline, morpholine, N,N,N',N'-tetramethyldiaminomethane, N-methylmorpholine, ethylenediamine, 1-methylpiperidine, 1-methylpyrrolidine, 1,4-diazabicyclo[2.2.2]octane and 1,4-dimethylpiperazine. Preferred solvents include xylene, triethylamine, pyridine, N,N-dimethylformamide, butyl acetate, N,N,N',N'-tetramethylethylenediamine, N,N,N',N'-tetramethyldiaminomethane, N-methylmorpholine, 4-picoline, pyrrolidine, ethylenediamine, 1-methylpiperidine, 1-methylpyrrolidine, 1,4-diazabicyclo [2.2.2]octane, 1,4-dimethylpiperazine and morpholine. Preferred solvents of the amine type include N,N,N',N'-tetramethylethylenediamine, 4-picoline, N-methylmorpholine and N,N,N',N'-tetramethyldiaminometlhane.

If a solvent is used, the amount of solvent is not critical, provided the mixture is fluid. In some cases, it may be preferred that the amount of solvent be at least 25 volume percent, based on the combined volume of the solvent and the carboxylic acid, dicarboxylic acid or aqueous acid. This may be required, for example, if the reaction mixture is not fluid under reaction conditions or if the halogenated aromatic compounds are not soluble. A solvent as listed above may also be added to the reaction mixture after the reaction is substantially completed. In addition, the use of a solvent may reduce the amount of the copper containing dehalogenation agent required. For example, the use of an amine containing solvent or a polymeric amine in a conventional solvent in addition to a carboxylic acid may result in the need for as little as 0.01 equivalent of a copper containing dehalogenation agent as compared to about 1.0 equivalent or more of a copper containing delhalogenation agent when a carboxylic acid solvent such as propionic acid is used without an additional amine containing solvent.

Equipment used in carrying out the method of the present invention should include a mechanism for agitation and a heating means. For example, a round bottom flask equipped with a condenser and a magnetic stir bar may be used or a reaction kettle with an overhead stirrer may be used.

The following examples and experimental procedures are provided for guidance to the practitioner and are not meant to limit the scope of the invention which is defined by the claims.

EXAMPLE 1

Dehalogenation of Methyl 2,5-Dichloro-4-methylbenzoate

A 50-mL round-bottom flask was equipped with a magnetic stir bar, reflux condenser, thermometer, nitrogen inlet, and heating mantle attached to a temperature controller. The flask was charged with methyl 2,5-diclhloro-4-methylbenzoate (4.0 g, 18.3 mmol) and copper powder (2.32 g, 36.5 mmol). Propionic acid (6 mL) and xylenes (10 mL) were added, and the resulting mixture was heated to 130°–135° C. The reaction was monitored by gas chromatographic (GC) analysis and was judged to be complete when the starting material was no longer detectable (11 hours). The reaction mixture was cooled to room temperature and filtered; the solids were washed with xylenes. The filtrates were blue-green. The filtrates were combined and washed with 1 molar (M) hydrochloric acid solution until the blue-green color disappeared. The resulting yellow organic layer was washed with water and dried over sodium sulfate. The solvent was removed by evaporation under reduced pressure. The residue was dried under vacuum to afford 3.14 g of methyl 3-chloro-4-methylbenzoate. The product was a pale yellow solid, melting point (mp) 27°–28° C.

EXAMPLE 2

Dehalogenation of Methyl 2,5-Dichlorobenzoate

A 50-mL round-bottom flask was equipped with a magnetic stir bar, reflux condenser, thermometer, nitrogen inlet, and heating mantle attached to a temperature controller. The flask was charged with methyl 2,5-dichlorobenzoate (5.0 g, 24 mmol) and copper powder (3.04 g, 48 mmol). Propionic acid (10 mL) and xylenes (15 mL) were added, and the resulting mixture was heated to 130°–135° C. The reaction was monitored by GC analysis and was judged to be complete when the starting material was no longer detectable (3 hours). The reaction mixture was cooled to room temperature and filtered; the solids were washed with xylenes. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum, yielding 3.93 g of methyl 3-chlorobenzoate as a pale yellow oil.

EXAMPLE 3

Dehalogenation of 2,4-Dichlorobenzamide

A 50-mL round-bottom flask was equipped with a magnetic stir bar, reflux condenser, thermometer, nitrogen inlet, and heating mantle attached to a temperature controller. The flask was charged with 2,4-dichlorobenzamide (5.0 g, 26 mmol) and copper powder (3.34 g, 52 mmol). Propionic acid (15 mL) was added, and the resulting mixture was heated to 130°–135° C. The reaction was monitored by GC analysis and was judged to be complete when the starting material was no longer detectable (0.5 hour). As the reaction mixture was cooled, a mixture of xylenes (30 mL) was added. The resulting mixture was filtered, and the solids were washed with xylenes. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum to give 2.91 g of the expected 4-chlorobenzamide as an off-white solid, mp 160°–165° C.

EXAMPLE 4

Dehalogenation of 2,4-Dichloroacetoplhenone under Varying Reaction Conditions a) Using Copper Powder and Propionic Acid A 50-mL round-bottom flask was equipped with a magnetic stir bar, reflux condenser, thermometer, nitrogen inlet, and heating mantle attached to a temperature controller. The flask was charged with 2,4-dichloroacetoplhenone (5.0 g, 20.5 mmol) and copper powder (3.36 g, 53 mmol). Propionic acid (15 mL) was added, and the resulting mixture was heated to 130°–135° C. The reaction was monitored by GC analysis and was judged to be complete when the starting material was no longer detectable (2 hours). As the reaction mixture was cooled, a mixture of xylenes (15 mL) was added. The resulting mixture was filtered, and the solids were washed with xylenes. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum, yielding 3.38 g of 4-chloroacetophenone as a yellow oil.

b) Using Copper(I) Oxide and Propionic Acid

A 100-mL round-bottom flask was equipped with a magnetic stir bar, reflux condenser, thermometer, nitrogen inlet, and heating mantle attached to a temperature controller. The flask was charged with 2,4-dichloroacetoplhenone (5.0 g, 26.5 mmol) and copper(I) oxide (7.6 g, 52.9 mmol). Propionic acid (15 mL) was added, and the resulting mixture was heated to 130° C. Additional copper(I) oxide (0.76 g, 5,3 mmol) was added after 2.5 hours in order to complete the dehalogenation. The reaction was monitored by GC analysis and was judged to be complete when the starting material was no longer detectable (3.5 hours). As the reaction mixture was cooled, toluene (25 mL) was added. The resulting mixture was filtered, and the solids were washed with toluene. The filtrates were blue-green. The filtrates were combined and washed with 2M hydrochloric acid solution (2×50 mL) until the blue-green color disappeared. The resulting yellow organic layer was washed with water (50 mL) and dried over sodium sulfate. The solvent was removed by evaporation under reduced pressure. The residue was dried under vacuum, yielding 3.76 g of 4-chloroacetophenone as a yellow oil.

c) Using Copper Powder, Triethylamine and Acetic Acid

A 100-mL round-bottom flask was equipped with a magnetic stir bar, reflux condenser, thermometer, nitrogen inlet, and heating mantle attached to a temperature controller. The flask was charged with 2,4-dichloroacetophenone (5.0 g, 26.5 mmol) and copper powder (0.84 g, 13.2 mmol). The flask was purged with nitrogen for 0.5 hour. Meanwhile, a separate flask was charged with acetic acid (30 g) and triethylamine (30 g). The resulting solution was degassed by bubbling nitrogen through the solution for 0.5 hour. A portion of the degassed solution (20 mL) was charged to the reaction flask by syringe and the resulting mixture was heated to 135° C. Additional copper (0.17 g, 2.65 mmol) was added after 2 hours in order to complete the dehalogenation. The reaction was monitored by GC analysis and was judged to be complete when the starting material was no longer detectable (5 hours). The reaction mixture was cooled to room temperature and poured into a 250-mL Erlenmeyer flask; toluene (50 mL) and 2M hydrochloric acid solution (50 mL) were added. The resulting mixture was filtered, and the solids were washed with toluene. The resulting brown organic layer was washed with 2M hydrochloric acid solution (50 mL), water (50 mL), and 5% sodium hydroxide solution (50 mL). Solids precipitated during the base wash. The mixture was filtered through a pad of Florisil® (magnesium silicate), which was rinsed with additional toluene. The filtrates were combined to give a yellow solution. The solvent was removed by evaporation under reduced pressure. The residue was dried under vacuum, yielding 3.38 g of 4-chloroacetophenone as a brown oil.

d) Using Copper Powder, Pyridine and Acetic Acid

A 50-mL round-bottom flask was equipped with a magnetic stir bar, reflux condenser, thermometer, nitrogen inlet, and heating mantle attached to a temperature controller. The flask was charged with 2,4-diichloroacetophenone (5.0 g, 26.5 mmol) and copper powder (1.68 g, 26.5 mmol). The flask was purged with nitrogen for 0.5 hour. Meanwhile, a separate flask was charged with acetic acid (15 g) and pyridine (15 g). The resulting solution was degassed by bubbling nitrogen through the solution for 0.5 hour. A portion of the degassed solution (20 mL) was charged to the reaction flask by syringe; the resulting mixture was heated to 130° C. Additional copper (0.50 g, 7.87 mmol) was added after 3 hours in order to complete the dehalogenation. The reaction was monitored by GC analysis and was judged to be complete when the starting material was no longer detectable (5 hours). The reaction mixture was cooled to room temperature, and toluene (25 mL) was added. The resulting mixture was filtered through a pad of Florisile (magnesium silicate), which was then rinsed with additional toluene. The filtrates were blue-green. The filtrates were combined and washed with 2M hydrochloric acid solution (2×50 mL) until the blue-green color disappeared. The resulting yellow-brown organic layer was washed with 5% sodium hydroxide solution (50 mL) and water (75 mL). The solution was dried over sodium sulfate. The solvent was removed by evaporation under reduced pressure. The residue was dried under vacuum, yielding 3.87 g of 4-chloroacetophenone as a brown oil.

e) Using Copper(I) Chloride, N,N-Dimethylformamide and Propionic Acid

A 50-mL round-bottom flask was equipped with a magnetic stir bar, reflux condenser, thermometer, nitrogen inlet, and heating mantle attached to a temperature controller. The flask was charged with 2,4-diclhloroacetophlenone (5.0 g, 26.5 mmol) and copper(I) chloride (5.24 g, 53.0 mmol). Propionic acid (5.87 g, 79.0 mmol) and N,N-dimethylformamide (20 mL) were added, and the resulting mixture was heated to 130°–135° C. Additional copper(I) chloride was added after 31 hours in order to increase the rate of the reaction. The reaction was monitored by GC analysis and was judged to be complete when the starting material was no longer detectable (100 hours). The reaction mixture was cooled to room temperature; toluene (50 mL) and 2M hydrochloric acid solution (100 mL) were added. The layers were separated, and the upper organic layer was washed with 2M hydrochloric acid solution (50 mL). The resulting yellow organic layer was washed with water (50 mL) and dried over sodium sulfate. The solvent was removed by evaporation under reduced pressure. The residue was dried under vacuum, yielding 3.95 g of 4-chloroacetophenone (3.95 g, 98.9%) as a yellow oil.

EXAMPLE 5

Dehalogenation of 2,3-Dichlorobenzoic Acid

A 50-mL round-bottom flask was equipped with a magnetic stir bar, reflux condenser, thermometer, nitrogen inlet, and heating mantle attached to a temperature controller. The flask was charged with 2,3-dichlorobenzoic acid (4.55 g, 23.8 mmol) and copper powder (3.02 g, 47.6 mmol). Propionic acid (30 mL) was added, and the resulting mixture was heated to 130°–135° C. The reaction was monitored by GC analysis and was judged to be complete when the starting material was no longer detectable (1 hour). Ethyl acetate (30 mL) was added as the reaction mixture was cooled to room temperature. The resulting mixture was filtered, and the solids were washed with ethyl acetate. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum to afford 3.55 g of 3-chlorobenzoic acid as a pale yellow solid, mp 153°–153.5° C.

EXAMPLE 6

Dehalogenation of 2-Chloroacetophenone

A 50-mL round-bottom flask was equipped with a magnetic stir bar, reflux condenser, thermometer, nitrogen inlet, and heating mantle attached to a temperature controller. The flask was charged with 2-chloroacetophenone (5.0 g, 32.3 mmol) and copper powder (4.1 g, 64.7 mmol). Propionic acid (20 mL) was added, and the resulting mixture was heated to 130° C. The reaction was monitored by GC analysis and was judged to be complete when the starting material was no longer detectable (2.5 hours). Ethyl acetate (20 mL) was added as the reaction mixture was cooled to room temperature. The mixture was filtered, and the solids were washed with ethyl acetate. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum to give 3.20 g of the expected acetophenone as a pale yellow oil. The gas chromatogram of the product matched that of a commercial standard.

EXAMPLE 7

Dehalogenation of 2,6-Dichlorobenzoic Acid

A 100-mL round-bottom flask was equipped with a magnetic stir bar, reflux condenser, thermometer, nitrogen inlet, and heating mantle attached to a temperature controller. The flask was charged with 2,6-dichlorobenzoic acid (5.0 g, 26.2 mmol) and copper powder (3.3 g, 78.6 mmol). Pivalic acid (15 mL) was added, and the resulting mixture was heated to 130°–135° C. The reaction was monitored by GC analysis and was judged to be complete when the starting material was no longer detectable (3 hours). Ethyl acetate (50 mL) was added as the reaction mixture was cooled to room temperature. The resulting mixture was filtered, and the solids were washed with ethyl acetate. The filtrates were blue-green. The filtrates were combined and washed with 1M hydrochloric acid solution until the blue-green color disappeared. The resulting pale tan organic layer was washed with water and dried over sodium sulfate. The solvent was removed by evaporation under reduced pressure. The residue was dried under vacuum, affording 2.89 g of benzoic acid as an off-white solid, mp 118°–119° C.

EXAMPLE 8

Preparation of Methyl 3,4,5-Trichlorobenzoate from Methyl 4-Chlorobenzoate

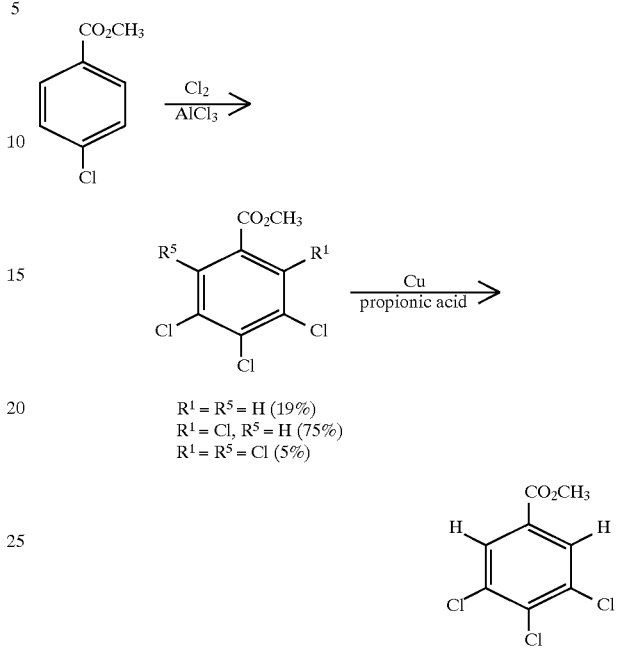

$R^1 = R^5 = H$ (19%)
$R^1 = Cl, R^5 = H$ (75%)
$R^1 = R^5 = Cl$ (5%)

a) Chlorination of Methyl 4-Chlorobenzoate

A 250-mL round-bottom flask was equipped with a magnetic stir bar, reflux condenser, thermometer, nitrogen inlet, heating mantle attached to a temperature controller, and connections to a chlorine tank and caustic scrubber. Methyl 4-chlorobenzoate (10.0 g, 58.6 mmol), 1,2-dichloroethane (125 mL), and aluminum trichloride (10.2 g, 76.2 mmol) were charged to the flask. The reaction mixture was maintained at ambient temperature as chlorine was bubbled in through a 3/16" ID Teflon® tube placed just above the magnetic stir bar. The reaction was monitored by GC analysis; it was judged to be complete when the 3,4-dichloro ester had disappeared. The reaction mixture was poured into a chilled solution of 2M hydrochloric acid solution (100 mL). The resulting mixture was in two layers. The lower organic layer was washed with water and dried over sodium sulfate solution. The solvent was removed by evaporation under reduced pressure. The residual white solid (15.5 g) consisted of a mixture of methyl 3,4,5-trichlorobenzoate (19%), methyl 2,3,4,5-tetrachlorobenzoate (75%), and methyl 2,3,4,5,6-pentachlorobenzoate (5%). Based on the relative percentages of each component in the gas chromatogram, the yield was estimated to be 98%.

b) Dehalogenation

A 50-mL round-bottom flask was equipped with a magnetic stir bar, reflux condenser, thermometer, nitrogen inlet, and heating mantle attached to a temperature controller. The flask was charged with the chlorinated ester mixture generated above (5.0 g, approx. 18.7 mmol) and copper powder (2.32 g, 36.4 mmol). Propionic acid (15 mL) was added, and the resulting mixture was heated to 130°–135° C. The reaction was monitored by GC analysis and was judged to be complete when the tetrachloro ester starting material was no longer detectable (3 hours). Toluene was added to the reaction mixture as it was cooled to room temperature. The resulting mixture was filtered, and the solids were washed with toluene. The filtrates were blue-green. The filtrates were combined and washed with 1M hydrochloric acid solution until the blue-green color disappeared. The resulting colorless organic layer was washed with water and dried over sodium sulfate. The solvent was removed by evaporation under reduced pressure. The residue was dried under vacuum, affording 4.13 g of methyl 3,4,5-trichlorobenzoate as a white solid, mp 111°–112° C.

EXAMPLE 9

Preparation of Methyl 3,5-Dichlorobenzoate from Methyl 4-Bromobenzoate

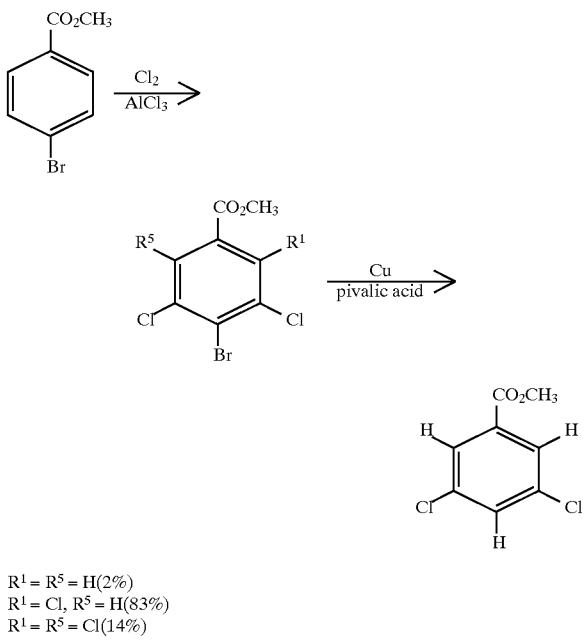

$R^1 = R^5 = H(2\%)$
$R^1 = Cl, R^5 = H(83\%)$
$R^1 = R^5 = Cl(14\%)$ a) Chlorination of Methyl 4-Bromobenzoate A 100-mL round-bottom flask was equipped with a magnetic stir bar, reflux condenser, thermometer, nitrogen inlet, heating mantle attached to a temperature controller, and connections to a chlorine tank and caustic scrubber. Methyl 4-bromobenzoate (6.0 g, 27.9 mmol), 1,2-dichloroethane (60 mL), and aluminum trichloride (4.65 g, 34.9 mmol) were charged to the flask. The reaction mixture was maintained at ambient temperature as chlorine was bubbled in through a 3/16" ID Teflon® tube placed just above the magnetic stir bar. After 2 hours, 1.0 g additional aluminum trichloride was added in order to increase the reaction rate. The reaction was monitored by GC analysis and was judged to be complete when the 3,5-dichloro ester constituted less than 3% of the reaction mixture. The reaction mixture was poured into a chilled solution of 2M hydrochloric acid solution (100 mL). The reaction mixture was in two layers. The lower organic layer was washed with water and dried over sodium sulfate solution. The solvent was removed by evaporation under reduced pressure. The residual cream-colored solid (9.0 g) consisted of a mixture of methyl 4-bromo-3,5-dichlorobenzoate (2%), methyl 4-bromo-2,3,5-trichlorobenzoate (83%), and methyl 4-bromo-2,3,5,6-tetrachlorobenzoate (14%). Based on the relative percentages of each component in the gas chromatogram, the yield was estimated to be 97%.

b) Dehalogenation

A 50-mL round-bottom flask was equipped with a magnetic stir bar, reflux condenser, thermometer, nitrogen inlet, and heating mantle attached to a temperature controller. The flask was charged with the mixture of chlorinated esters generated above (5.0 g, approx. 15.8 mmol) and copper powder (2.0 g, 31.4 mmol). Pivalic acid (15 mL) was added, and the resulting mixture was heated to 135° C. Additional copper (1.0 g, 15.7 mmol) was added after 1, 5, 9, and 13 hours in order to complete the reaction. Additional solvents were added in order to maintain the fluidity of the reaction mixture. At 5 hours, 15 mL pivalic acid was added. At 9 hours and 13 hours, a mixture of xylenes (15 mL) was added. The reaction was monitored by GC analysis and was judged to be complete when the trichloro and tetrachloro esters were no longer detectable. The total reaction time was 15 hours. The reaction mixture was cooled to room temperature. The mixture was filtered, and the solids were washed with xylenes. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum, affording 3.20 g of the desired methyl 3,5-dichlorobenzoate as a pale yellow solid, mp 24°–27° C.

EXAMPLE 10

Dehalogenation of 2,5-Dichlorobenzoic Acid

A 100-mL round-bottom flask was equipped with a magnetic stir bar, reflux condenser, thermometer, nitrogen inlet, and heating mantle attached to a temperature controller. The flask was charged with 2,5-dichlorobenzoic acid (5.0 g, 26.2 mmol) and copper powder (5.0 g, 78.5 mmol). Sulfuric acid (98%; 35 mL) was added, and the resulting mixture was heated to 130°–135° C. Additional copper (0.83 g, 13.1 mmol) was added after 1 hour in order to complete the delhalogenation. The reaction was monitored by GC analysis and was judged to be complete when the starting material was no longer detectable (1.5 hours). The reaction mixture was cooled to room temperature and transferred to a 500-mL Erlenmeyer flask. Water (100 mL) and toluene (100 mL) were added. The resulting mixture was filtered and the solids were washed with toluene. The filtrates were blue-green. The filtrates were combined and washed with 1M hydrochloric acid solution until the blue-green color disappeared. The resulting pale tan organic layer was washed with water and dried over sodium sulfate. The solvent was removed by evaporation under reduced pressure. The residue was dried under vacuum, affording 3.49 g of 3-chlorobenzoic acid as a white solid, mp 152°–153° C.

EXAMPLE 11

Preparation of Methyl 5-Bromo-3-chloro-4-methylbenzoate from Methyl 3-Chloro-4-methylbenzoate

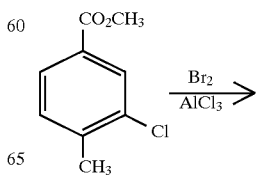

-continued

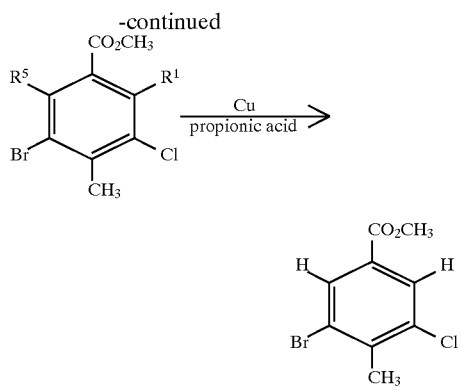

$R^1 = R^5 = H(9\%)$
$R^1 = Br, R^5 = H(58\%)$
$R^1 = R^5 = Br(33\%)$ a) Bromination of Methyl 3-Chloro-4-methylbenzoate A 100-mL round-bottom flask was equipped with a magnetic stir bar, reflux condenser, thermometer, nitrogen inlet, heating mantle attached to a temperature controller, and connections to a chlorine tank and caustic scrubber. Methyl 3-chloro-4-methylbenzoate (10.0 g, 54.1 mmol), 1,2-dichloroethane (65 mL), and aluminum trichloride (13.2 g, 98.8 mmol) were charged to the flask. The reaction mixture was maintained at 55°–60° C. as bromine (15.1 g, 94.6 mmol) was added to the reaction mixture. The reaction was monitored by GC analysis and was judged to be complete when the starting material had disappeared. The reaction mixture was poured into a chilled solution of 3M hydrochloric acid solution (300 mL). The reaction mixture was in two layers. The upper aqueous layer was extracted with 1,2-dichloroethane. The combined organic layers were washed with saturated sodium thiosulfate solution and water, then dried over sodium sulfate. The solvent was removed by evaporation under reduced pressure. The residual cream-colored solid (17.19 g) consisted of a mixture of methyl 3-bromo-5-chloro-4-methylbenzoate (9%), methyl 2,5-dibromo-3-chloro-4-methylbenzoate (58%), and methyl 2,3,6-tribromo-5-chloro-4-methylbenzoate (33%). Based on the relative percentages of each component in the gas chromatogram, the yield was estimated to be 89%.

b) Dehalogenation

A 50-mL round-bottom flask was equipped with a magnetic stir bar, reflux condenser, thermometer, nitrogen inlet, and heating mantle attached to a temperature controller. The flask was charged with the chlorinated ester mixture generated above (4.0 g, approx. 11.2 mmol) and copper powder (1.94 g, 31.0 mmol). Propionic acid (20 mL) was added, and the resulting mixture was heated to 130° C. Additional copper (1.0 g, 15.7 mmol) was added to the reaction in three portions (after 1.5, 2.5, and 3.5 hours) in order to complete the dehalogenation. The reaction was monitored by GC analysis and was judged to be complete when the tribromo and dibromo esters were no longer detectable (4.5 hours). Ethyl acetate (20 mL) was added as the reaction mixture was cooled to room temperature. The resulting mixture was filtered, and the solids were washed with ethyl acetate. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum, affording 2.45 g of methyl 3-bromo-5-chloro-4-methylbenzoate as a pale tan solid, mp 53°–55° C.

EXAMPLE 12

Preparation of Ethyl 4-Chloro-3-fluorobenzoate from 2,4-Dichloro-5-fluorobenzoyl Chloride a) Esterification of 2,4-Dichloro-5-fluorobenzoyl Chloride A 25-mL round-bottom flask was equipped with a magnetic stir bar, thermometer, nitrogen inlet, addition funnel, and a reflux condenser. The flask was charged with 2,4-dichloro-5-fluorobenzoyl chloride (5.38 g, 23.65 mmol) and ethyl ether (5.0 g). The resulting colorless solution was cooled to 17° C. using a cool water bath. Ethanol (3.20 g, 69.47 mmol; absolute grade) was added dropwise from the addition funnel over ten minutes. Once the addition was complete, the solution was warmed to room temperature and stirred overnight (17 hours). Additional ether (20 mL) was added to the reaction mixture, which was then transferred to a separatory funnel. The reaction mixture was washed twice with 2% sodium hydroxide solution (10 mL), then with water (10 mL). The upper organic layer was separated and dried over sodium sulfate. The solvent was removed by evaporation under reduced pressure. The residue was dried in a vacuum oven to give 5.09 g of ethyl 2,4-dichloro-5-fluorobenzoate as a pale yellow oil.

b) Dehalogenation

A 50-mL round-bottom flask was equipped with a magnetic stir bar, reflux condenser, thermometer, nitrogen inlet, and heating mantle attached to a temperature controller. The flask was charged with ethyl 2,4-dichloro-5-fluorobenzoate (5.09 g, 21.4 mmol) and copper powder (2.72 g, 42.8 mmol). Propionic acid (10 mL) was added, and the resulting mixture was heated to 135° C. The reaction was monitored by GC analysis and was judged to be complete when the starting material was no longer detectable (5 hours). Toluene (25 mL) was added as the reaction was cooled to room temperature. The resulting mixture was filtered, and the solids were washed with toluene. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum to give 2.97 g of ethyl 4-chloro-3-fluorobenzoate as a pale yellow oil.

EXAMPLE 13

Preparation of Methyl 2-Chloro-6-fluorobenzoate from 2-Chloro-6-fluorobenzoic Acid a) Esterification of 2-Chloro-6-fluorobenzoic Acid A 50-mL round-bottom flask was equipped with a magnetic stir bar, reflux condenser, thermometer, nitrogen inlet, and a heating mantle attached to a temperature controller. The flask was charged with 2-chloro-6-fluorobenzoic acid (8.30 g, 47.55 mmol), methanol (15 g), and concentrated sulfuric acid (1 g). The reaction mixture was heated to 60° C. for seven days, then cooled to room temperature. Ethyl ether (50 mL) was added; the reaction mixture was transferred to a separatory funnel and washed with 1M sodium hydroxide solution (3×40 mL), then with water (40 mL). The organic layer was dried over sodium sulfate. The solvent was removed by evaporation under reduced pressure and the residue was dried under vacuum to give 5.34 g of methyl 2-chloro-6-fluorobenzoate as a yellow oil.

b) Dehalogenation

A 50-mL round-bottom flask was equipped with a magnetic stir bar, reflux condenser, thermometer, nitrogen inlet, and heating mantle attached to a temperature controller. The flask was charged with methyl 2-chloro-6-fluorobenzoate (5.11 g, 27.1 mmol) and copper powder (3.44 g, 54.2 mmol). Propionic acid (15 mL) was added, and the resulting mixture was heated to 135° C. Additional copper (0.34 g) was added after 7 hours in order to complete the dehalogenation. The reaction was monitored by GC analysis and was judged to be complete when the starting material was no longer detectable (10.5 hours). Toluene (30 mL) was added as the reaction was cooled to room temperature. The resulting mixture was filtered, and the solids were washed with toluene. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried under vacuum to give 3.54 g of methyl 2-fluorobenzoate as a pale yellow oil. Some of the product appeared to be lost during vacuum drying due to vaporization.

EXAMPLE 14

Preparation of Methyl 3,5-Dichloro-4-methylbenzoate from Methyl 4-Methylbenzoate

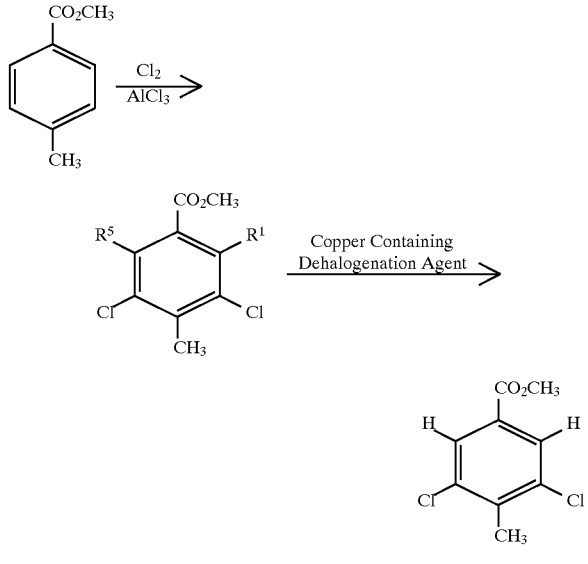

$R^1 = R^5 = H(2\%)$
$R^1 = Cl, R^5 = H(79\%)$
$R^1 = R^5 = Cl(19\%)$ a) Chlorination of methyl 4-methylbenzoate A 100-mL round-bottom flask was equipped with a magnetic stir bar, reflux condenser, thermometer, nitrogen inlet, heating mantle attached to a temperature controller, and connections to a chlorine tank and caustic scrubber. Methyl 4-methylbenzoate (10.0 g, 66.6 mmol), 1,2-dichloroethane (40 g), and aluminum trichloride (11.0 g, 79.9 mmol) were added to the flask. The reaction mixture was maintained at 60° C. as chlorine was bubbled in through a ³⁄₁₆" ID Teflon® tube placed just above the magnetic stir bar. The reaction was monitored by GC analysis and was judged to be complete when the 3-chloro ester and 2,5-diclhloro esters disappeared. The reaction mixture was poured into a chilled solution of 1M hydrochloric acid solution (100 mL). The reaction mixture was in two layers. The lower organic layer was washed with water and dried over sodium sulfate solution. The solvent was removed by evaporation under reduced pressure. The residual cream-colored solid (15.1 g) consisted of a mixture of methyl 3,5-dichloro-4-methylbenzoate (2%), methyl 2,3,5-trichloro-4-methylbenzoate (79%), and methyl 2,3,5,6-tetrachloro-4-methylbenzoate (19%). Based on the relative percentages of each component in the gas chromatogram, the yield was estimated to be 87%.

b) Dehalogenation Using Copper Powder and Propionic Acid

A 50-mL round-bottom flask was equipped with a magnetic stir bar, reflux condenser, thermometer, nitrogen inlet, and heating mantle attached to a temperature controller. The flask was charged with the chlorinated ester mixture generated above (3.0 g, approx. 11.6 mmol) and copper powder (1.53 g, 24 mmol). Propionic acid (10 mL) was added, and the resulting mixture was heated to 130°–135° C. The reaction was monitored by GC analysis and was allowed to run overnight (21.5 hours). The reaction was judged to be complete when the tetrachloro ester starting material was no longer detectable. A mixture of xylenes was added to the reaction mixture as it was cooling to room temperature. The mixture was filtered and the solids were washed with xylenes. The filtrates were blue-green. The filtrates were combined and washed with 1M hydrochloric acid solution until the blue-green color disappeared. The resulting pale yellow organic layer was washed with water and dried over sodium sulfate. The solvent was removed by evaporation under reduced pressure. The residue was dried under vacuum, affording 2.43 g of methyl 3,5-dichloro-4-methylbenzoate as a pale yellow solid, mp 47.5°–48.5° C.

c) Dehalogenation Using Copper Powder, Triethylamine and Acetic Acid

A 50-mL round-bottom flask was equipped with a magnetic stir bar, reflux condenser, thermometer, nitrogen inlet, and heating mantle attached to a temperature controller. The flask was charged with 5.0 g (~20.1 mmol) of a mixture of chlorinated esters containing methyl 2,3,5,6-tetrachloro-4-methylbenzoate (12%), methyl 2,3,5-trichloro-4-methylbenzoate (70%), methyl 3,5-diclhloro-4-methylbenzoate (12%), methyl 2,5-dichloro-4-methylbenzoate (2%) and methyl 3-chloro-4-methylbenzoate (2%). Copper powder (0.75 g, 11.8 mmol) was added, and the reaction flask was flushed with nitrogen. Meanwhile, a solution of acetic acid (20 g) and triethylamine (10 g) was prepared in a separate flask. The solution was degassed over 0.5 hour by introducing a stream of nitrogen at the bottom of the flask through a needle. The degassed solution was introduced to the reaction flask via syringe. The resulting mixture was heated to 135° C. and the reaction progress was monitored by GC analysis. The reaction was judged to be complete when the starting material was no longer detectable (14 hours).

The reaction mixture was cooled to room temperature. Water (500 mL) was added and the resulting mixture was extracted with toluene (100 mL). The upper organic layer was separated and 2M hydrochloric acid (200 mL) was added to it. A dark-colored precipitate appeared and the solid was removed by filtration. The filtrate was washed with 5% sodium hydroxide solution (200 mL). A white solid precipitated which was removed by filtration. The resulting organic layer was washed with 200 mL water and dried over sodium sulfate. The solvent was removed by evaporation under reduced pressure. The residue was dried in a vacuum oven and afforded 3.32 g of methyl 3,5-dichloro-4-methylbenzoate as a pale yellow solid.

d) Dehalogenation Using Copper Powder and Propionic Acid

A 50-mL round-bottom flask was equipped with a magnetic stir bar, reflux condenser, thermometer, nitrogen inlet, and heating mantle attached to a temperature controller. The flask was charged with 98% pure methyl 2,3,5-trichloro4-methylbenzoate (5.0 g, 19.7 mmol) and copper powder (2.55 g, 39.5 mmol). Propionic acid (15 mL) was added and the resulting mixture was heated to 130°–135° C. The reaction was monitored by GC analysis. The reaction was judged to be complete when the starting material was no longer detectable (3 hours).

A mixture of xylenes (20 mL) was added to the reaction mixture as it cooled to room temperature. The mixture was filtered, and the solids were washed with xylenes. The filtrates were blue-green. The filtrates were combined and washed with 1M hydrochloric acid solution until the blue-green color disappeared. The resulting yellow organic layer was washed with water and dried over sodium sulfate. The solvent was removed by evaporation under reduced pressure. The residue was dried in a vacuum oven to give 3.78 g of methyl 3,5-dichloro-4-methylbenzoate as a pale yellow solid.

e) Dehalogenation Using Copper(I) Oxide and Propionic Acid

A 50-mL round-bottom flask was equipped with a magnetic stir bar, reflux condenser, thermometer, nitrogen inlet and heating mantle attached to a temperature controller. The flask was charged with 98% pure methyl 2,3,5-trichloro-4-methylbenzoate (5.0 g, 19.7 mmol), copper(I) oxide (5.63 g, 39.4 mmol) and propionic acid (20 mL). The resulting mixture was heated to 135° C. Additional copper(I) oxide (2.11 g, 14.8 mmol) was charged during the reaction in order to complete the dehalogenation. The reaction was monitored by GC analysis. The reaction was judged to be complete when the starting material was no longer detectable (10 hours).

Toluene (15 mL) was added to the reaction mixture as it cooled to room temperature. The mixture was filtered, and the solids were washed with toluene. The filtrates were blue-green. The filtrates were combined and washed with 1M hydrochloric acid solution until the blue-green color disappeared. The resulting pale yellow organic layer was washed with water and dried over sodium sulfate. The solvent was removed by evaporation under reduced pressure. The residue was dried under vacuum, affording 3.8 g of methyl 3,5-dichloro-4-metlhylbenzoate as a pale yellow solid.

EXAMPLE 15

Mixture Purification Using Copper(II) Acetate and an Amine Solvent

A 100-mL round-bottom flask was equipped with a magnetic stir bar, reflux condenser, thermometer, nitrogen inlet and heating mantle attached to a temperature controller. The flask was charged with a 5.0 g (~23.0 mmol) of a mixture of chlorinated acids containing 2,3,5-trichloro-4-methylbenzoic acid (57%), 3,5-dichloro-4-methylbenzoic acid (22%), 2,5-dichloro-4-methylbenzoic acid (10%), 2,3-dichloro-4-methylbenzoic acid (1%) and 3-chloro-4-methylbenzoic acid (10%). Copper(II) acetate (2.82 g, 15.5 mmol), N,N,N',N'-tetramethylethylenediamine (7.21 g, 62.0 mmol), acetic acid (2.05 g) and n-butyl acetate (30 mL) were added. The resulting mixture was heated to 115° C. The reaction was monitored by GC analysis. The reaction was judged to be complete when the trichloro acid was no longer detectable (8 hours).

The reaction mixture was transferred to a separatory funnel and washed with 1M hydrochloric acid solution, then with water. The organic layer was dried over sodium sulfate. The solvent was removed by evaporation under reduced pressure. The residue was dried in a vacuum oven, affording 3.68 g of a mixture of 3,5-dichloro-4-methylbenzoic acid (81%) and 3-chloro-4-methiylbenzoic acid (19%) as a pale yellow solid.

EXAMPLE 16

Mixture Purification Using Copper Powder and an Amine Solvent

A 50-mL round-bottom flask was equipped with a magnetic stir bar, reflux condenser, thermometer, nitrogen inlet and heating mantle attached to a temperature controller. The flask was charged with a 5.0 g (~23.0 mmol) of a mixture of chlorinated acids containing 2,3,5-trichloro-4-methylbenzoic acid (54%), 3,5-dichloro-4-methylbenzoic acid (25%), 2,5-diclhloro-4-methylbenzoic acid (9%), 2,3-dichloro-4-methylbenzoic acid (1%), and 3-chloro-4-methylbenzoic acid (11%). Copper powder (0.12 g, 1.81 mmol), N,N,N',N'-tetramethylethylenediamine (12.5 mL), and acetic acid (12.5 mL) were added. The resulting mixture was heated to 135° C. The reaction was monitored by GC analysis. The reaction was judged to be complete when the trichloro acid was no longer detectable (9 hours).

Methyl isobutyl ketone (70 mL) was added to the reaction mixture. The resulting solution was transferred to a separatory funnel and washed with 1M hydrochloric acid solution and with water. The organic layer was dried over sodium sulfate. The solvent was removed by evaporation under reduced pressure. The residue was dried in a vacuum oven and afforded 3.92 g of a mixture of 3,5-dichloro-4-methylbenzoic acid (83%) and 3-chloro-4-methylbenzoic acid (17%) as a pale yellow solid.

EXAMPLE 17

Mixture Purification Using Copper Powder and an Amine Solvent

A 100-mL round-bottom flask was equipped with a magnetic stir bar, reflux condenser, thermometer, nitrogen inlet and heating mantle attached to a temperature controller. The flask was charged with 5.0 g (~22.1 mmol) of a mixture of chlorinated acids containing 2,3,5-trichloro-4-methylbenzoic acid (72%), 3,5-dichloro-4-methylbenzoic acid (15%), 2,5-dichloro-4-methylbenzoic acid (7%) and 3-chloro-4-methylbenzoic acid (6%). Copper powder (0.27 g, 4.36 mmol), 4-methylpyridin (12.5 mL) and acetic acid (12.5 mL) were added. The resulting mixture was heated to 135° C. The reaction was monitored by GC analysis. The reaction was judged to be complete when the trichloro acid was no longer detectable (7 hours).

Methyl isobutyl ketone (70 mL) was added to the reaction mixture. The resulting solution was transferred to a separatory funnel and washed with 1M hydrochloric acid solution and with water. The organic layer was dried over sodium sulfate. The solvent was removed by evaporation under reduced pressure. The residue was dried in a vacuum oven, affording 4.05 g of a mixture of 3,5-dichloro-4-methylbenzoic acid (91%) and 3-chloro-4-methylbenzoic acid (9%) as a pale yellow solid.

It is to be understood that changes and variations in this invention may be made without departing from the spirit and scope of this invention as defined by the appended claims.

We claim:

1. A method for preparing an aryl or a heteroaryl compound by selectively removing halogen atoms from a halogenated aryl or heteroaryl compound through heating a reaction mixture comprising (i) at least one aryl or heteroaryl compound possessing a Z directing group and one or two halo groups independently selected from chloro, bromo and iodo which are ortho to said Z group, or a further substituted aryl or heteroaryl compound possessing a Z directing group and one or two halo groups independently selected from chloro, bromo and iodo which are ortho to said Z group, (ii) from about 0.01 to about 5.0 molar equivalents, per equivalent of halo group to be removed, of a copper containing dehalogenation agent, and (iii) at least about 1.0 molar equivalent, per equivalent of halo group to be removed, of one or more acids selected from the group consisting of aliphatic $(C_1-C_{10})$ carboxylic acids, aliphatic $(C_2-C_{10})$dicarboxylic acids, aryl carboxylic acids, aryl dicarboxylic acids, aqueous inorganic acids, sulfonic acids and mixtures thereof; wherein the Z directing group is $CO_2R^{10}$, $CONR^{11}R^{12}$, $COR^{13}$ or cyano, $R^{10}$, $R^{11}$ and $R^{12}$ are each independently a hydrogen atom, $(C_1-C_6)$alkyl, aryl or substituted aryl, and $R^{13}$ is a hydrogen atom, $(C_1-C_6)$alkyl, substituted $(C_1-C_6)$alkyl, aryl or substituted aryl.

2. The method of claim 1 wherein the aryl or heteroaryl compound, possessing a Z directing group and one or two halo groups independently selected from chloro, bromo and iodo which are ortho to said Z group, is phenyl, 1-naphthyl, 2-naphthyl, anthryl, phenanthryl, thienyl, furyl, pyrrolyl, triazolyl, thiazolyl, oxazolyl, isoxazolyl, thiazolyl, isothiazolyl, pyridyl, pyrimidinyl, pyrazinyl, pyridazinyl, triazinyl, benzofuranyl, benzothienyl, indolyl, quinazolinyl, acridinyl, purinyl or quinoxalinyl; or the further substituted aryl or heteroaryl compound, possessing a Z directing group and one or two halo groups independently selected from chloro, bromo and iodo which are ortho to said Z group, is phenyl, 1-naphthyl, 2-naphthyl, anthryl, phenanthryl, thienyl, furyl, pyrrolyl, triazolyl, thiazolyl, oxazolyl, isoxazolyl, thiazolyl, isothiazolyl, pyridyl, pyrimidinyl, pyrazinyl, pyridazinyl, triazinyl, benzofuranyl, benzothienyl, indolyl, quinazolinyl, acridinyl, purinyl or quinoxalinyl.

3. The method of claim 2 wherein the aryl or compound is a substituted phenyl having the formula (I)

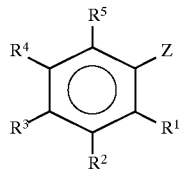

wherein $R^1$, $R^2$, $R^3$, $R^4$ and $R^5$ are each independently a hydrogen atom, $(C_1-C_8)$alkyl, substituted $(C_1-C_8)$alkyl, $(C_3-C_6)$cycloalkyl, substituted $(C_3-C_6)$cycloalkyl, aryl, substituted aryl, $CH2OR^6$, $NR^7R^{10}$, $OR^8$, $SR^9$, heteroaryl, substituted heteroaryl, fluoro, chloro, bromo or iodo, provided that at least one of $R^1$ and $R^5$ is chloro, bromo or iodo, the Z directing group is $CO_2R^{10}$, $CONR^{11}R^{12}$, $COR^{13}$ or cyano, $R^6$, $R^8$ and $R^9$ are each independently a hydrogen atom, $(C_1-C_6)$alkyl, aryl, substituted aryl or $COR^{14}$, $R^7$, $R^{10}$, $R^{11}$ and R12 are each independently a hydrogen atom, $(C_1-C_6)$alkyl, aryl or substituted aryl, $R^{13}$ is a hydrogen atom, $(C_1-C_6)$alkyl, substituted $(C_1-C_6)$alkyl, aryl or substituted aryl, and $R^{14}$ is $(C_1-C_6)$alkyl or aryl.

4. The method of claim 3 wherein $R^1$ and $R^5$ are each independently a hydrogen atom, $(C_1-C_8)$alkyl, substituted $(C_1-C_8)$alkyl, aryl, substituted aryl, fluoro, chloro, bromo or iodo, provided that at least one of $R^1$ and $R^5$ is chloro, bromo or iodo, $R^2$, $R^3$ and $R^4$ are each independently a hydrogen atom, $(C_1-C_8)$alkyl, aryl, substituted $(C_1-C_8)$alkyl, substituted aryl, $NR^7R^{10}$, fluoro, chloro or bromo, Z is $CO_2R^{10}$, $CONR^{11}R^{12}$ or $COR^{13}$, $R^7$ and $R^{10}$ are each independently a hydrogen atom, $(C_1-C_6)$alkyl, aryl or substituted aryl, $R^{11}$ and $R^{12}$ are each independently $(C_1-C_6)$alkyl, aryl or substituted aryl and $R^{13}$ is $(C_1-C_6)$alkyl, substituted $(C_1-C_6)$alkyl, aryl or substituted aryl.

5. The method of claim 4 wherein $R^1$ and $R^5$ are each independently a hydrogen atom, $(C_1-C_8)$alkyl, chloro or bromo, provided that at least one of $R^1$ and $R^5$ is chloro or bromo, $R^2$, $R^3$ and $R^4$ are each independently a hydrogen atom, $(C_1-C_8)$alkyl, aryl, fluoro, chloro or bromo, Z is $CO_2R^{10}$ and $R^{10}$ is a hydrogen atom, $(C_1-C_6)$alkyl, aryl or substituted aryl.

6. The method of claim 1 wherein the copper containing dehalogenation agent is copper metal or a copper(I) compound.

7. The method of claim 6 wherein the copper(I) compound is copper(I) chloride, copper(I) bromide or copper(I) oxide.

8. The method of claim 6 wherein the amount of copper metal or copper(I) compound is from about 1.0 to about 3.0 equivalents per equivalent of halo group to be removed.

9. The method of claim 1 wherein the reaction mixture further comprises a solvent.

10. The method of claim 9 wherein the solvent is xylene, toluene, ethyl acetate, butyl acetate, mesitylene, octane, decane, anisole, nitrobenzene, methoxyethyl ether, dimethyl sulfoxide, N,N-dimethylformamide, pyridine, pyrrolidine, 2-pyrrolidinone, pyrrole, piperidine, piperazine, quinoline, acetonitrile, valeronitrile, triethylamine, triisobutylamine, tripropylamine, diisopropylamine, chlorobenzene, dichlorobenzene, N,N,N',N'-tetramethylethylenediamine, 4-picoline, morpholine, N,N,N',N'-tetramethyldiaminomethane, N-methylmorpholine, ethylenediamine, 1-methylpiperidine, 1-methylpyrrolidine, 1,4-diazabicyclo[2.2.2]octane or 1,4-dimethylpiperazine.

11. The method of claim 10 wherein the solvent is xylene, triethylamine, pyridine, N,N-dimethylformamide, butyl acetate, N,N,N',N'-tetramethylethylenediamine, N,N,N',N'-tetramethyldiaminomethane, N-methylmorpholine, 4-picoline, pyrrolidine, ethylenediamine, 1-methylpiperidine, 1-methylpyrrolidine, 1,4-diazabicyclo[2.2.2]octane, 1,4-dimethylpiperazine or morpholine.

12. The method of claim 9 wherein the solvent is an amine or a solvent in the presence of a polymeric amine.

13. The method of claim 12 wherein the amine is N,N,N',N'-tetramethylethylenediamine, 4-picoline, N-methylmorpholinie or N,N,N',N'-tetramethyldiaminomethane.

14. The method of claim 12 wherein the polymeric amine is poly(4-vinylpyridine).

15. The method of claim 1 or 9 wherein the reaction mixture is heated to a reaction temperature of from 95° C. to 220° C.

16. The method of claim 1 or 9 wherein the one or more acids are selected from the group consisting of aliphatic ($C_1$–$C_{10}$) carboxylic acids having the formula $R^{15}CO_2H$ wherein $R^{15}$ is a hydrogen atom or ($C_1$–$C_9$)alkyl, aliphatic ($C_2$–$C_{10}$) dicarboxylic acids having the formula $HO_2C(CHR^{16})_nCO_2H$ wherein $R^{16}$ is a hydrogen atom when n is 0–8 or ($C_1$–$C_7$)alkyl when n is 1, benzoic acid, 1-naphthoic acid, 2-naphthoic acid, 9-phenanthroic acid, phthalic acid, isophthalic acid, terephthalic acid, naphthalenedicarboxylic acid, benzenesulfonic acid, p-toluenesulfonic acid, methanesulfonic acid, ethanesulfonic acid, 1-naphthalenesulfonic acid, 2-naphthalenesulfonic acid, aqueous hydrochloric acid and aqueous sulfuric acid.

17. The method of claim 16 wherein the one or more acids are selected from the group consisting of formic acid, acetic acid, propionic acid, valeric acid, pivalic acid, oxalic acid, succinic acid, malonic acid and aqueous sulfuric acid.

18. The method of claim 17 wherein the one or more acids are selected from the group consisting of acetic acid, propionic acid and pivalic acid.

19. The method of claim 12 wherein the copper containing dehalogenation agent is copper metal, a copper(I) compound or a copper(II) compound.

20. The method of claim 19 wherein the copper(I) compound is copper(I) chloride, copper(I) bromide or copper(I) oxide.

21. The method of claim 19 wherein the copper(II) compound is copper(ll) acetate, copper(II) chloride, copper (II) bromide, copper(II) oxide or copper(II) sulfate.

22. The method of claim 19 wherein the amount of copper metal, copper(I) compound or copper(II) compound is from about 0.01 to about 2.0 equivalents of copper per equivalent of halo group to be removed.

23. The method of claim 22 wherein the amount of copper metal, copper(I) compound or copper(II) compound is from about 0.1 to about 1.0 equivalent of copper per equivalent of halo group to be removed.

\* \* \* \* \*